US008029532B2

(12) United States Patent
Sirota (10) Patent No.: US 8,029,532 B2
(45) Date of Patent: Oct. 4, 2011

(54) CLOSURE DEVICE WITH BIOMATERIAL PATCHES

(75) Inventor: Daniel J. Sirota, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 832 days.

(21) Appl. No.: 11/869,499

(22) Filed: Oct. 9, 2007

(65) Prior Publication Data

US 2008/0091235 A1   Apr. 17, 2008

Related U.S. Application Data

(60) Provisional application No. 60/851,119, filed on Oct. 11, 2006.

(51) Int. Cl.
*A61B 17/08* (2006.01)
(52) U.S. Cl. ....................................................... 606/213
(58) Field of Classification Search .................. 606/151, 606/157, 200, 213, 232, 217, 218
See application file for complete search history.

(56) References Cited

U.S. PATENT DOCUMENTS

| | | | |
|---|---|---|---|
| 4,917,089 A | 4/1990 | Sideris | |
| 5,108,420 A | 4/1992 | Marks | |
| 5,171,259 A | 12/1992 | Inoue | |
| 5,257,637 A | 11/1993 | El Gazayerli | |
| 5,284,488 A | 2/1994 | Sideris | |
| 5,334,217 A | 8/1994 | Das | |
| 5,433,727 A | 7/1995 | Sideris | |
| 5,545,178 A | 8/1996 | Kensey et al. | |
| 5,601,576 A | 2/1997 | Garrison | |
| 5,643,317 A | 7/1997 | Pavcnik et al. | |
| 5,662,681 A | 9/1997 | Nash et al. | |
| 5,855,614 A | 1/1999 | Stevens et al. | |
| 5,879,366 A | 3/1999 | Shaw et al. | |
| 5,947,997 A | 9/1999 | Pavcnik et al. | |
| 5,993,844 A | 11/1999 | Abraham et al. | |
| 6,080,182 A * | 6/2000 | Shaw et al. ................... | 606/213 |
| 6,117,160 A | 9/2000 | Bonutti | |
| 6,206,931 B1 | 3/2001 | Cook et al. | |
| 6,358,284 B1 | 3/2002 | Fearnot et al. | |
| 6,488,706 B1 | 12/2002 | Solymar | |
| 6,508,828 B1 | 1/2003 | Akerfeldt et al. | |
| 6,572,650 B1 | 6/2003 | Abraham et al. | |
| 6,712,837 B2 | 3/2004 | Akerfeldt et al. | |
| 6,726,920 B1 | 4/2004 | Theeuwes et al. | |

(Continued)

OTHER PUBLICATIONS

Sideris et al., "Transvenous Atrial Septal Defect Occlusion in Piglets With a 'Buttoned' Double-Disk Device", Circulation, vol. 81, No. 1, pp. 312-318, Jan. 1990.

(Continued)

*Primary Examiner* — Tuan V. Nguyen
(74) *Attorney, Agent, or Firm* — Brinks Hofer Gilson & Lione (57) ABSTRACT

A closure device includes a bioremodelable patch and a joining element linking one or more bioremodelable patches to tissue portions adjacent to a bodily opening. The closure device may include a pair of bioremodelable patches linked by sutures and compressively joined to overlapping tissue portions adjacent to the opening. The closure device may be further contained within an assembly additionally including a catheter having a hollow sheath and a pusher. The pusher may be used to dislodge one or more bioremodelable patches from the catheter to facilitate stable closure of a bodily opening, such as a septal opening in a PFO.

9 Claims, 7 Drawing Sheets

U.S. PATENT DOCUMENTS

| | | |
|---|---|---|
| 6,949,116 B2 | 9/2005 | Solymar et al. |
| 2002/0183787 A1 | 12/2002 | Wahr et al. |
| 2002/0198563 A1 | 12/2002 | Gainor et al. |
| 2003/0028213 A1 | 2/2003 | Thill et al. |
| 2003/0144694 A1 | 7/2003 | Chanduszko et al. |
| 2003/0206860 A1 | 11/2003 | Bleyer et al. |
| 2003/0208232 A1 | 11/2003 | Blaeser et al. |
| 2004/0093025 A1 | 5/2004 | Egnelov |
| 2004/0098042 A1 | 5/2004 | Devellian et al. |
| 2004/0133236 A1 | 7/2004 | Chanduszko |
| 2005/0070923 A1 | 3/2005 | McIntosh |
| 2005/0096696 A1 | 5/2005 | Forsberg |
| 2005/0209636 A1 * | 9/2005 | Widomski et al. ............ 606/213 |
| 2005/0234509 A1 | 10/2005 | Widomski et al. |
| 2005/0251206 A1 | 11/2005 | Maahs et al. |
| 2005/0256532 A1 | 11/2005 | Nayak et al. |
| 2005/0273124 A1 | 12/2005 | Chanduszko |
| 2005/0288706 A1 | 12/2005 | Widomski et al. |
| 2006/0217760 A1 | 9/2006 | Widomski et al. |

OTHER PUBLICATIONS

Das et al., "Experimental Atrial Septal Defect Closure With a New, Transcatheter, Self-Centering Device", Circulation, vol. 88, No. 4, Pt. 1, pp. 1754-1764, Oct. 1993.

Jux et al., "A New Biological Matrix for Septal Occlusion", J. Interv. Cardiol., vol. 16, No. 2, pp. 149-152, Apr. 2003.

Hara et al., "Patent Foramen Ovale: Current Pathology, Pathophysiology, and Clinical Status", J. Am. Coll. Cardiol., vol. 46, No. 9, pp. 1768-1776, Nov. 1, 2005.

Jux et al., "Interventional Atrial Septal Defect Closure Using a Totally Bioresorbable Occluder Matrix", vol. 48, No. 1, pp. 161-169, Jul. 4, 2006.

* cited by examiner

CLOSURE DEVICE WITH BIOMATERIAL PATCHES

This application claims the benefit of priority under 35 U.S.C. §119(e) to U.S. Provisional Application No. 60/851,119, filed Oct. 11, 2006, which is hereby incorporated by reference in its entirety.

BACKGROUND

A patent foramen ovale (PFO) is a persistent, one-way, usually flap-like opening in the wall between the right atrium 10 and left atrium 12 of the heart. In utero, the foramen ovale serves as a physiologic conduit for right-to-left shunting of blood in the fetal heart. Because blood is oxygenated through the umbilical chord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure presses the septum primum against the walls of the septum secundum, covering the foramen ovale and resulting in functional closure of the foramen ovale. This closure is usually followed by anatomical closure of the foramen ovale due to fusion of the septum primum to the septum secundum.

Where anatomical closure of the foramen ovale does not occur, a PFO is created. Studies have shown that a relatively large percentage of adults have a PFO. The presence of a PFO is generally considered to have no therapeutic consequence in otherwise healthy adults. Because left atrial (LA) pressure is normally higher than right atrial (RA) pressure, the flap usually stays closed. Under certain conditions, however, right atrial pressure can exceed left atrial pressure, creating the possibility that blood could pass from the right atrium to the left atrium and blood clots could enter the systemic circulation. It is desirable that this circumstance be eliminated.

Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. It has been estimated that in 50% of cryptogenic strokes, a PFO is present. In addition, there is significant evidence that patients with a PFO who have had a cerebral vascular event are at increased risk for future, recurrent cerebrovascular events.

Patients suffering a cryptogenic stroke or a transient ischemic attack (TIA) in the presence of a PFO often are considered for medical therapy to reduce the risk of a recurrent embolic event. Accordingly, patients at such an increased risk are considered for prophylactic medical therapy to reduce the risk of a recurrent embolic event. These patients are commonly treated with oral anticoagulants to reduce the risk of a recurrent embolic event. However, these anticoagulants have potentially adverse side effects, including hemorrhaging, hematoma, and adverse interactions with other drugs. In addition, use of anticoagulant drugs can alter a person's recovery and necessitate adjustments in a person's daily living pattern.

Where anticoagulation is contraindicated, surgery may be employed to close a PFO. The surgery would typically include suturing a PFO closed by attaching septum secundum to septum primum. Like other open surgical treatments, however, this surgery is highly invasive, risky, requires general anesthesia, and may result in lengthy recuperation.

Nonsurgical closure of PFOs has become possible with the introduction various mechanical closure devices, including umbrella devices and the like, which were initially for percutaneous closure of atrial septal defects (ASDs; a condition where there is not a septum primum). These devices potentially allow patients to avoid the side effects often associated with anticoagulation therapies and the risks of invasive surgery.

However, devices for treating heart defects, such as PFO and other atrial and ventricular septal heart defects have their share of drawbacks. The complex anatomical features of PFOs present a challenge to a one size fits all approach. The PFO involves two components, septum primum and septum secundum. The septum secundum is thicker than septum primum and exhibits limited mobility and compliance. Failure of these two structures to fuse creates a tunnel-like opening, the PFO. The distance of the nonfusion between the two septa determines the particular size of the PFO, which must be considered in the design of a device targeting PFOs. Nevertheless, devices are often configured so that the patient's anatomy must be adjusted to fit the geometry of the device. As a consequence, heart tissue may be torn when accommodating such devices.

Conventional nonsurgical closure devices are often technically complex, bulky, have a high septal profile, and are difficult to deploy in a precise location or reposition when necessary. In addition, the large masses of foreign material often accompanying the device may lead to unfavorable body adaptation to the device, which result in thromboses or other unfavorable reactions. Moreover, many devices are set apart by a relatively long central section corresponding to the PFO tunnel. By increasing the device profile, the device can present difficulties with respect to complete endothelialization. Additionally, many of the devices have a geometry which tends to prevent the device from remaining flat against, or within the defect once deployed. Further drawbacks to nonsurgical closure devices include complications resulting from fractures of the components, conduction system disturbances, perforations of heart tissue, and residual leaks.

Accordingly, there is a need for improved closure devices limiting the amount of foreign material deployed and increasing closure stability. The present invention is designed to address a number of the deficiencies surrounding conventional closure devices.

SUMMARY

A closure device includes one or more bioremodelable patches and one or more joining element(s) linking the bioremodelable patches to tissue portions adjacent to a bodily opening where closure is desired. In a particular aspect, the closure device includes a pair of bioremodelable patches and at least two knotted sutures linking the bioremodelable patches to one another and to overlapping tissue portions adjacent to a septal opening in the heart. Such a device may be used to stably close a PFO in the atrial septum of a heart.

In a further aspect, the present invention provides a closure device assembly for delivering the closure device in a patient. The closure device assembly includes a catheter having a hollow sheath and an open distal end. A pusher is slidably disposed in the sheath, which houses one or more bioremodelable patches and one or more joining elements. The joining element(s) are configured to link the bioremodelable patch to a tissue portion adjacent to a bodily opening, such as a septal opening in the heart. The pusher is configured to dislodge the one or more bioremodelable patches and/or joining element(s) from the open distal end of the catheter near an opening to facilitate its closure.

In a further aspect, a method for closing a bodily opening in a patient is provided. The method includes providing a closure device assembly having a catheter with a hollow sheath, a pusher, and a closure device, the closure device including first and second bioremodelable patches and at least one joining element. The catheter is positioned through a bodily opening and the pusher is advanced to deliver the first bioremodelable patch proximate to a first side of the opening. The pusher is then further advanced to deliver the second bioremodelable patch proximate to the other side of the opening. Joining elements in the assembly are configured to connectively join the first and second bioremodelable patches, securing them to tissue portions surrounding the opening so as to close the opening. In a preferred embodiment, the method is used to close a PFO.

DETAILED DESCRIPTION

An improved bioremodelable patch device for closing bodily openings, including septal openings of the heart is provided. Without wishing to be bound by a particular theory or to in any way limit the scope of the appended claims and their equivalents, it is believed that incorporation of bioremodelable material capable of causing angiogenesis and replacement by host tissues according to the present invention provides a more stable and permanent closure relative, thereby addressing one or more limitations associated with conventional closure devices.

In order to provide a clear and consistent understanding of the specification and claims, the following definitions are provided.

As used herein, the terms "opening", "bodily opening", "passageway", and "bodily passageway" are interchangeably used to refer to a bodily opening, aperture, canal, conduit, or duct, including but not limited to septal openings, heart valves, blood vessels, vessel punctures, bile ducts, and the like.

The term "bioremodelable" refers to a natural or synthetic material capable of inducing angiogenesis and tissue remodeling in a subject or host. A bioremodelable material includes at least one bioactive agent capable of inducing angiogenesis or tissue remodeling. The bioactive agent(s) in the bioremodelable material may stimulate infiltration of native cells into an acellular matrix, and formation of new blood vessels (capillaries) growing into the matrix to nourish the infiltrating cells (angiogenesis). Additionally, the bioactive agent(s) may effect the degradation or replacement of the bioremodelable material by endogenous tissue. The bioremodelable material may include extracellular collagen matrix (ECM) material, including but not limited to submucosal tissue, such as small intestine submucosal (SIS) tissue, or it may include other natural non-submucosal tissue source materials capable of inducing angiogenesis and tissue remodeling in a host.

The term "bioremodelable patch" refers to a structure made from natural materials which is capable of being used to close, block or occlude an opening or passageway, including but not limited to PFOs, other atrial and ventricular septal heart defects, tissue openings, blood vessels, bile ducts, and the like. The bioremodelable patch may be substantially formed from bioremodelable material(s) or it may further include a unitary structural supporting member incorporating bioremodelable material(s). Exemplary supporting members include natural, synthetic, polymeric sheet materials, woven and nonwoven textile materials and the like.

The terms "angiogenesis and angiogenic" refer to bioremodelable properties defined by formation of capillaries or microvessels from existing vasculature in a process necessary for tissue growth, where the microvessels provide transport of oxygen and nutrients to the developing tissues and remove waste products.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers, such the lamina muscularis mucosa and the stratum compactum. A submucosal material may be a decellularized or acellular tissue, which means it is devoid of intact viable cells, although some cell components may remain in the tissue following purification from a natural source. Alternative embodiments (for example, fluidized compositions and the like) include submucosal material expressly derived from a purified submucosal matrix structure. Submucosal materials according to the present disclosure are distinguished from collagen materials in other occlusion devices that do not retain their native submucosal structures or that were not prepared from purified submucosal starting materials first removed from a natural submucosal tissue source.

The term "small intestinal submucosa" (SIS) refers to a particular submucosal tissue structure removed from a small intestine source, such as pig.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "radiopaque" refers to a non-toxic material capable of being monitored or detected during injection into a mammalian subject by, for example, radiography or fluoroscopy. The radiopaque material may be either water soluble or water insoluble. Examples of water soluble radiopaque materials include metrizamide, iopamidol, iothalamate sodium, iodomide sodium, and meglumine. Examples of water insoluble radiopaque materials include tantalum, tantalum oxide, and barium sulfate, which are commercially available in the proper form for in vivo use. Other water insoluble radiopaque materials include, but are not limited to, gold, tungsten, stainless steel, and platinum.

In one aspect, the present invention provides a closure device, including one or more bioremodelable patches and one or more joining element(s) linking the bioremodelable patch to tissue portions adjacent to a bodily opening. The closure device may include a plurality of bioremodelable patches linked to one another or to host tissue(s) by one or more joining elements so as to a close a septal opening in the heart. In a preferred embodiment, the one or more bioremodelable patches are adapted for keeping a PFO closed.

Figure 1:
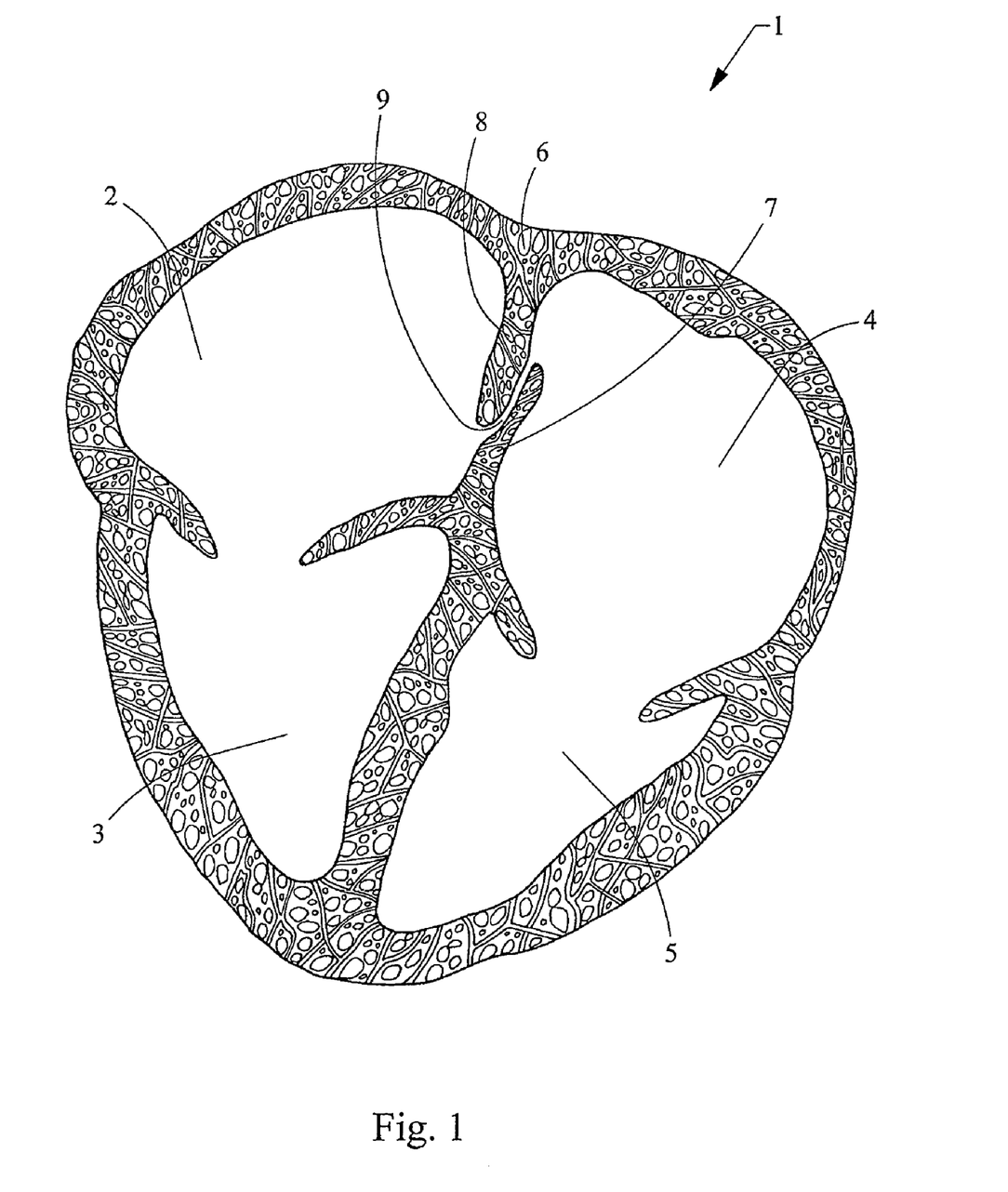
FIG. 1 illustrates is a cross-sectional view of a heart with a PFO.

FIG. 1 shows is a schematic front view of a heart 2 with a septal defect, such as patent foramen ovale (PFO). The heart 1 has a right atrium 2, right ventricle 3, left atrium 4, and a left ventricle 5. The septum 6 between the right atrium 2 and the left atrium 4 comprises a septum primum 7 and a septum secundum 8. The PFO 9 is an opening in the septum 6 that has not properly closed. Where a PFO 9 is present, the septum primum 7 typically overlaps the septum secundum 8 and the higher pressure in the left atrium 4 typically closes the flaps of the septum primum 7 and the septum secundum 8 so that blood does not leak between the atria 1 and 2. However, when there is a pressure change in the chest, the flaps may separate permitting blood to flow through the PFO and between the atria 1 and 2.

Figure 2A:
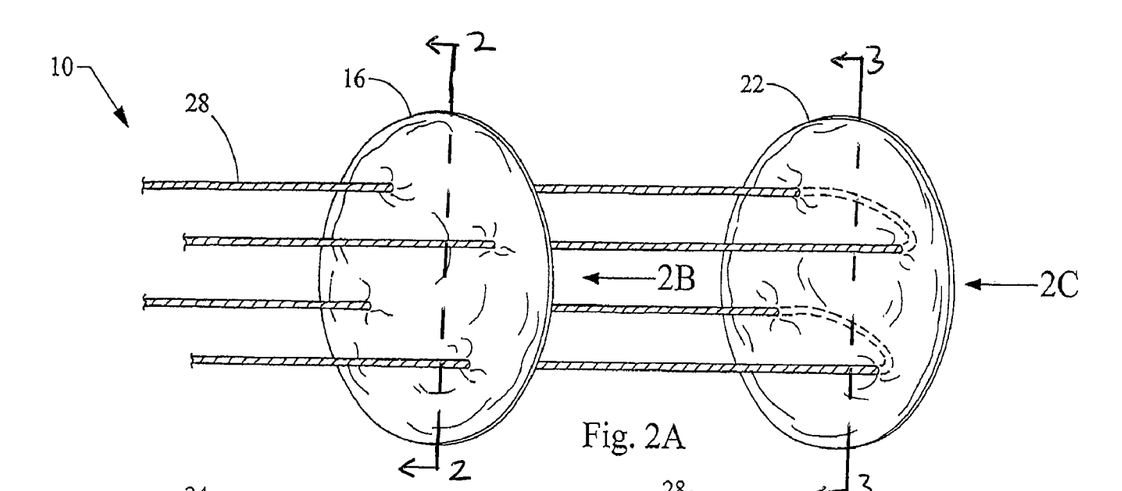
FIG. 2A illustrates an exemplary closure device according to an embodiment of the present invention.
Figure 2B:
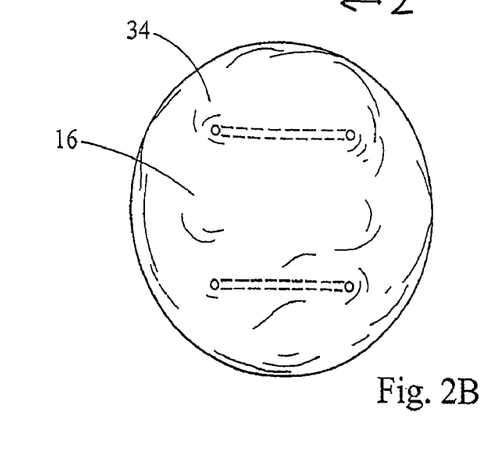
FIG. 2B is a view of FIG. 2A taken along line 2B.
Figure 2C:
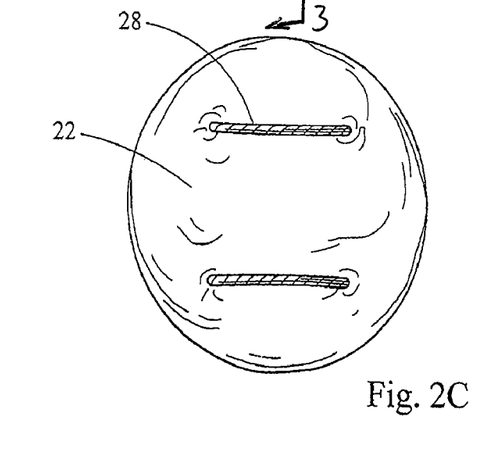
FIG. 2C is a view of FIG. 2A taken along line 2C.

FIG. 2A shows an exemplary closure device 10 depicting the bioremodelable patches as a pair of perforated patches 16 and 22 linked by a pair of joining elements depicted as sutures 28. FIG. 2B is a view taken along line 2-2 of FIG. 2A illustrating a proximal first patch 16 having two pairs of perforations 34. FIG. 2C is a view taken along line 3-3 illustrating a second patch 22 in which each pair of perforations is linked by a suture 28 connecting the first patch to the second patch.

Figure 3:
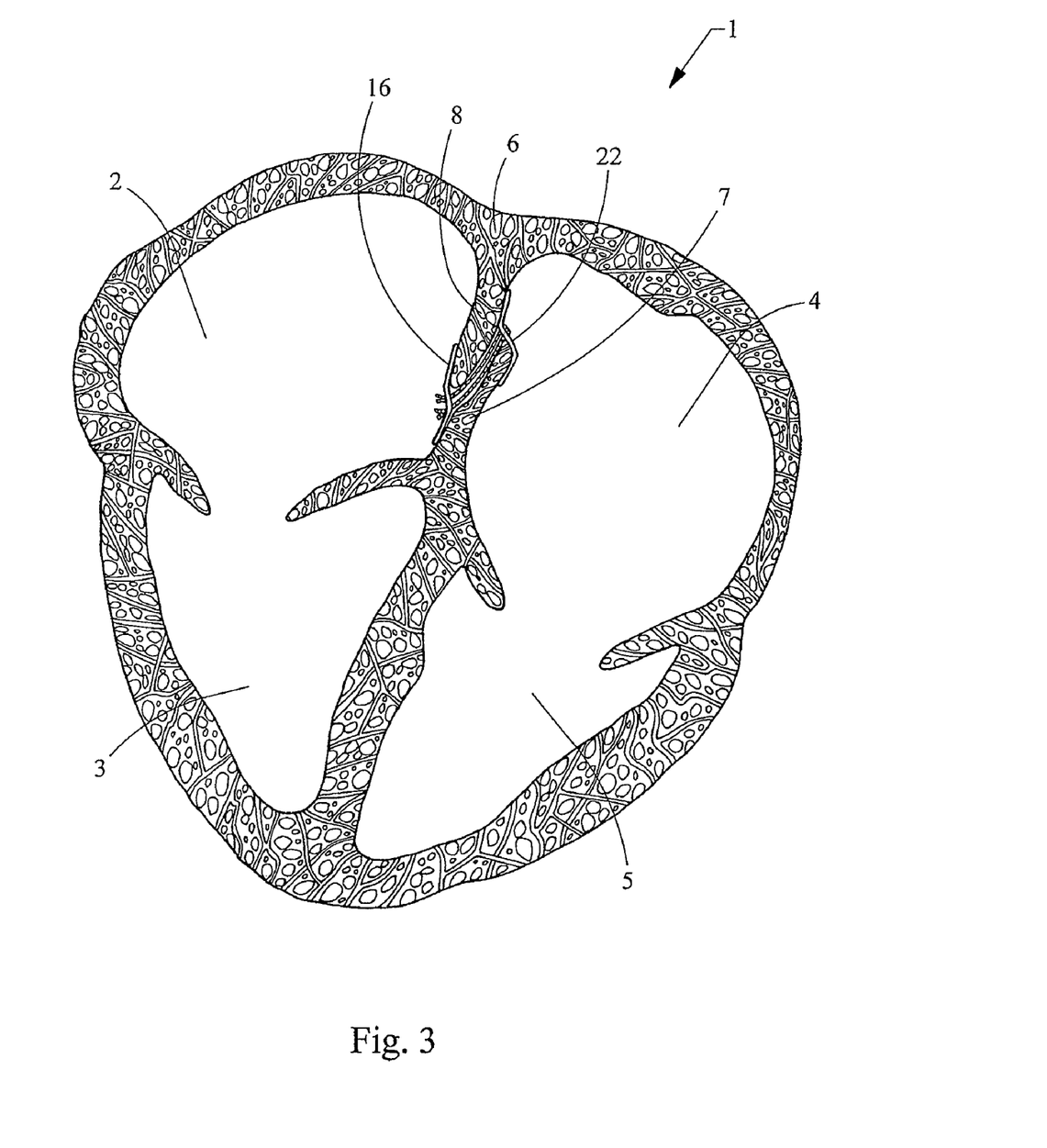
FIG. 3 illustrates a closure device positioned in a heart to close a PFO, according to an embodiment of the present invention.

FIG. 3 shows a closure device 10 positioned in a heart to close a PFO 9, according to an embodiment of the present invention. In FIG. 3, the closure device 10 is shown as patches 16 and 22 deployed on either side of a PFO 9 with sutures 28 passing through the PFO 9 opening and compressively joining the patches 16 and 22 to portions of the septum primum 7 and septum secundum 8. Upon suitable placement of the patches 16 and 22 to either side of the PFO 9, the sutures 28 can be pulled from the proximal end to closely join and knot the patches together, and to facilitate their attachment and eventual remodeling into the adjacent tissues on either side of the PFO 9, so as to permanently close the PFO 9. In other words, by suturing the patches 16 and 22 together, the patches 16 and 22 a compressive force is applied to the surrounding tissues 7 and 8, in this case a PFO 9, to facilitate stable closure thereof.

The bioremodelable patches provide a structural support suitable for sealing a bodily opening and preventing passage of blood or other substances therethrough. The bioremodelable patches are configured to adhere to opposing tissue structures surrounding the opening and to seal or block the opening. The bioremodelable patches can be configured to take on a variety of two dimensional and three dimensional shapes and geometric configurations suitable for sealing the opening. Preferably, the bioremodelable patches include flexible, elastic materials capable of being collapsed for passage through a catheter, but capable of returning to a shape or configuration suitable for closing a septal opening, such as a PFO.

Bioremodelable patches may shaped to cover or close any bodily passageway where occlusion is desired. In FIG. 2A, each bioremodelable patch includes a substantially flat surface structure having an area larger than the opening of the PFO 9, whereby outer portions in each bioremodelable patch are designed for attachment to tissues 7 and 8 at opposite sides of the PFO 9. FIG. 2A depicts a pair of bioremodelable patches in the form of circular bioremodelable patches 16 and 22. Flat bioremodelable patches or patches may be formed in a variety of shapes suitable for closing a bodily opening, including but not limited to square, oval, rectangular, cruciform, hexagonal and the like.

One or more bioremodelable patches may be joined to patient tissues surrounding the passageway to facilitate its closure. In a preferred embodiment, each of a pair of bioremodelable patches is configured for joining to patient tissues on either side of a bodily passageway. Alternatively, a single bioremodelable patch may be joined to patient tissues on one side of the passageway using sutures, tissue adhesives, hook members, barbs, staples or other suitable joining means known in the art.

A bioremodelable patch may include or be formed bioremodelable material. The bioremodelable patch may further include natural, synthetic, and/or polymeric sheet materials, including woven (for example, knitted) and nonwoven textile materials and the like, which can provide a structural support for passageway closure. Exemplary textile and polymeric sheet materials are disclosed in U.S. Patent Application Publication No. 2007/0082021, which is incorporated by reference herein. The bioremodelable patch may additionally include other biocompatible materials shaped to cover or close the passageway. For example, the bioremodelable patch may further include shape memory materials, such as nitinol or thermally responsive wires, including those described in U.S. Pat. No. 5,108,420.

Preferably, the bioremodelable patch includes a bioremodelable material on at least a portion of its surface. More preferably, the entire surface of the bioremodelable patch is covered by a bioremodelable material. Still more preferably, the bioremodelable patch is substantially formed from bioremodelable material(s).

A bioremodelable patch according to the present invention is capable of inducing angiogenesis and endothelialization of the implanted closure device. In addition, the bioremodelable patch is capable of remodeling the surrounding tissues, such that upon implantation in a patient, the bioremodelable closure device is degraded and replaced by the patient's endogenous tissues. As a result of the bioremodelable device being remodeled by host tissues, the bodily opening becomes stably closed, obviating concerns about migration of the device, adverse patient reactions to foreign materials and the like.

The bioremodelable material may include reconstituted or naturally-derived collagenous materials. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. Commercially available ECM materials capable of remodeling to the qualities of its host when implanted in human soft tissues include porcine SIS material (Surgisis® line of SIS materials, Cook Biotech Inc., West Lafayette, Ind.) and bovine pericardium (Peri-Strips®, Synovis Surgical Innovations, St. Paul, Minn.).

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, and/or protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example, at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material (C. Heeschen et al., Nature Medicine 7 (2001), No. 7, 833-839). When combined with a fluorescence microangiography technique, this model can provide both quantitative and qualitative measures of angiogenesis into biomaterials (C. Johnson et al., Circulation Research 94 (2004), No. 2, 262-268).

In addition to, or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (for example, human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, for example, thrombin, fibrinogen, and the like. These substances may be applied to the ECM material as a premanufactured step, immediately prior to the procedure (for example, by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al., which is incorporated by reference herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example, less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

A preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants and better preserves the aseptic state and inherent biochemical form of the submucosa, thereby potentiating its beneficial effects. Alternatively, the ECM- or submucosa may be purified a process in which the sterilization step is carried out after delamination as described in U.S. Pat. Nos. 5,993,844 and 6,572,650.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

Following delamination, submucosa may be sterilized using any conventional sterilization technique including propylene oxide or ethylene oxide treatment and gas plasma sterilization. Sterilization techniques which do not adversely affect the mechanical strength, structure, and biotropic properties of the purified submucosa are preferred. Preferred sterilization techniques also include exposing the graft to ethylene oxide treatment or gas plasma sterilization. Typically, the purified submucosa is subjected to two or more sterilization processes. After the purified submucosa is sterilized, for example, by chemical treatment, the matrix structure may be wrapped in a plastic or foil wrap and sterilized again using electron beam or gamma irradiation sterilization techniques.

Bioremodelable materials according to the present invention may be isolated and used in the form of intact natural sheets and they may be optimally configured by stretching or by laminating together multiple pieces, layers or strips of submucosal tissue compressed under for example, dehydrating conditions in accordance with the teachings set forth in U.S. Pat. Nos. 6,206,931 and 6,358,284, incorporated by reference herein. The bioremodelable materials may also be reconstituted in the form of a foam, gel, sponge or plug. The reconstituted bioremodelable material may be affixed to one or more of the bioremodelable patch surfaces and/or sandwiched between one or two bioremodelable patches to facilitate rapid absorption of the closure device.

A closure device according to the present invention further includes joining elements linking or biasing the bioremodelable patches to one another and/or to overlapping tissue portions adjacent to the passageway. Suitable joining elements may include sutures, joints, tissue adhesives, clips, staples, needles, shape memory materials, tension forces, spring forces, and other mechanical fasteners and the like which are suitable for joining, locking or biasing bioremodelable patches to one another and/or to opposite sides of the passageway.

Sutures may be used to compressively link one or more bioremodelable patches to tissue portions adjacent to a target occlusion site. The patches may be joined by sutures extending through one or more perforations or holes in one or more patches. The bioremodelable patches may be compressively joined to a target occlusion site by knotting the sutures to at least one side of the patch or opening.

Sutures may be made from a variety of suture types, including braided or monofilament. Preferably, the sutures are made of absorbable and/or bioremodelable materials. More particularly, the sutures may be made from polyester, polypropylene, polyglycolic acid, nylon, silk or any of a variety of suture materials known in the art. The sutures may be treated or coated with radiopaque materials to facilitate visualization of the device by radiography or fluoroscopy. The sutures may also be coated with antibiotics or other antimicrobial agents. Exemplary suture material includes TEVDEK II®, a braided polyester suture material impregnated with polytetrafluoroethylene (PTFE), DEKLENE II®, a polypropylene monofilament suture material, and nylon monofilament suture material, all of which are manufactured by Genzyme Biosurgery of Cambridge, Mass.

Tissue adhesives may be used to secure a bioremodelable patches to one another or to tissues in a patient. An exemplary tissue adhesive is BioGlue® (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) Am. Fam. Physician 61:1383-1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); and Bioglass (U.S. Biomaterials, Alachua, Fla.); CoStasis (Cohesion Technologies). MedPro Month (1999) 9:261-262; and MedPro Month (2000) 10:86-91.

The tissue adhesive may be bioresorbable. A bioresorbable adhesive may be formed by forming intermacromolecular complexes of a carboxypolysaccharide and, optionally, a polyether, such as polyethylene oxide. The carboxypolysaccharide may be of any biocompatible sort, including but not limited to carboxymethyl cellulose (CMC), carboxyethyl cellulose, chitin, hyaluronic acid, starch, glycogen, alginate, pectin, carboxymethyl dextran, carboxymethyl chitosan, and glycosaminoglycans such as heparin, heparin sulfate, and chondroitin sulfate.

The adhesive in the bioremodelable patch may be covered by a release liner and/or be formulated with an adhesive ready for attachment upon contact. Alternatively, an adhesive patch may be formulated such that upon hydration and contact with the organ surface, it can adhere to the patient tissue.

The above described adhesives may also be used in conjunction with other joining elements, including sutures, to facilitate securement of joining elements, including sealing of knots or loose suture ends, or joining of patches to one another and/or to a patient's tissue. Alternative methods for securing joining elements to one another or to patient tissues include, but are not limited to, stapling, crimping (including crimping of knots and/or loose suture ends with malleable metal pieces), use of chemical cross-linking agents, tissue welding, heat welding, pressure welding, heat source, light source, radiofrequency, lasering, other energy sources, and the like.

Figure 4:
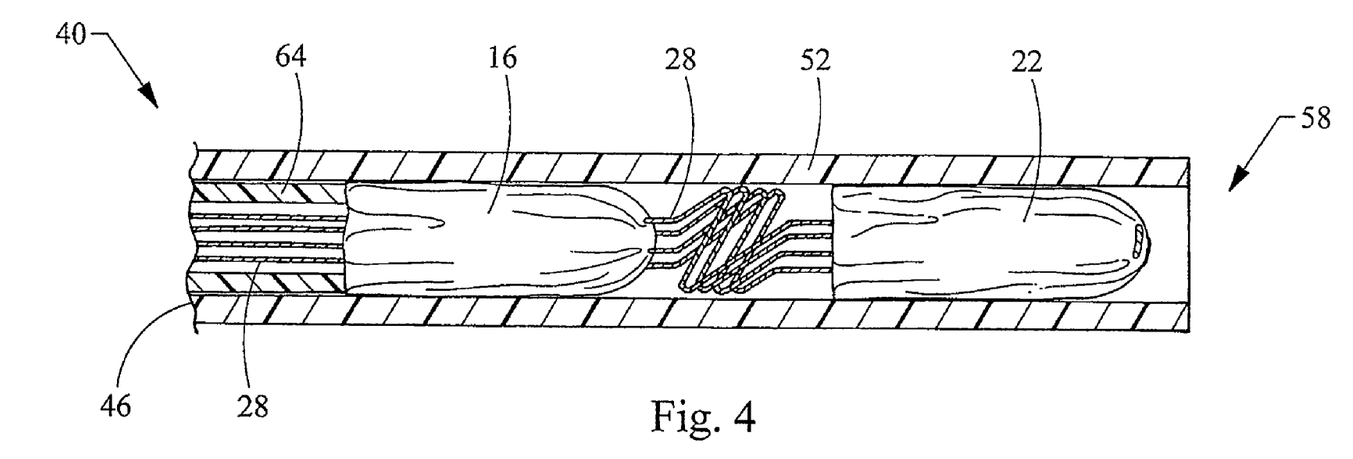
FIG. 4 illustrates a cross-sectional view of a closure device assembly according to an embodiment of the present invention.

In a further aspect, an assembly 40 for delivering the described closure device is provided. In FIG. 4, the assembly 40 includes a delivery catheter 46 having a hollow sheath 52 and an open distal end 58. The above-described bioremodelable patches 16 and 22 and joining elements 28 are co-disposed in the hollow sheath 52. The bioremodelable patches 16 and 22 may be joined to one or more joining elements 28 in a pre-assembled state, or they may be joined prior to or subsequent to deployment. Slidably disposed in the sheath is a pusher 64 coaxially associated with the delivery catheter 46.

The pusher 64 is configured to sequentially dislodge the bioremodelable patches 16 and 22 from the open distal end 58 upon advancement of the pusher 64 in the sheath 52. The pusher 64 includes a structure sufficiently housing one or more bioremodelable patches 16 and 22 to facilitate their coordinated dislodgement from the open distal end. The pusher 64 may have a uniform, substantially hollow or substantially filled structure configured for housing and displacing one or more bioremodelable patches.

In FIG. 4, a pair of bioremodelable patches 16 and 22 is disposed in the delivery catheter 46 in front of the pusher 64. In this example, the pusher 64 is a substantially hollow coaxially positioned structure directly engaging the proximal bioremodelable patch 16. Deployment of this assembly 40 requires advancement of the pusher 64 so that the proximal patch 16 pushes the distal patch 22 out of the distal end 58. Upon further advancement of the pusher 64, the proximal patch 16 is dislodged. Thus, the pusher 64 is configured to directly dislodge a first patch 16 and indirectly dislodge the other patch 22.

Figure 5A:
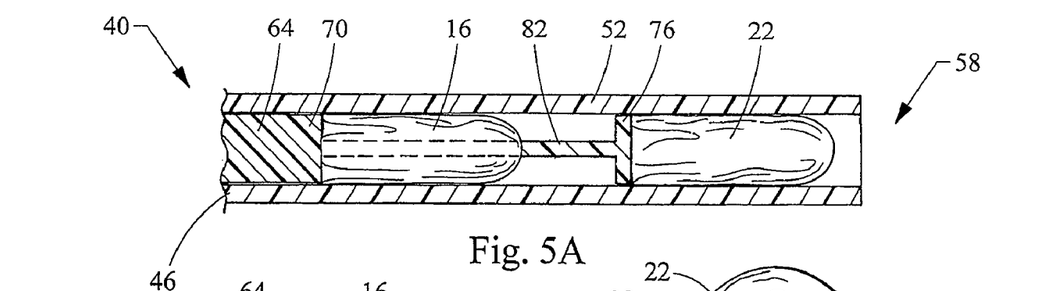
FIG. 5A illustrates a cross-sectional view of an exemplary closure device assembly according to another embodiment of the present invention.
Figure 5B:
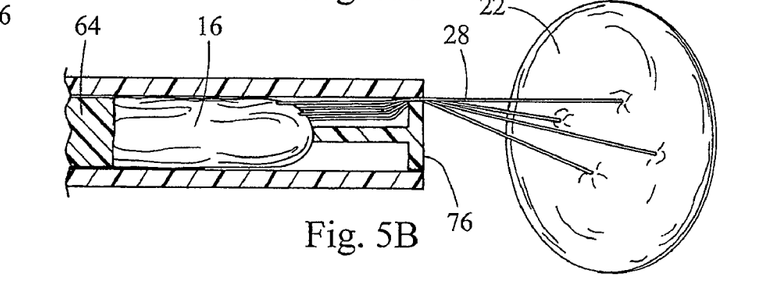
FIG. 5B illustrates the closure device assembly of FIG. 5A deploying a first bioremodelable patch according to an aspect of the present invention.
Figure 5C:
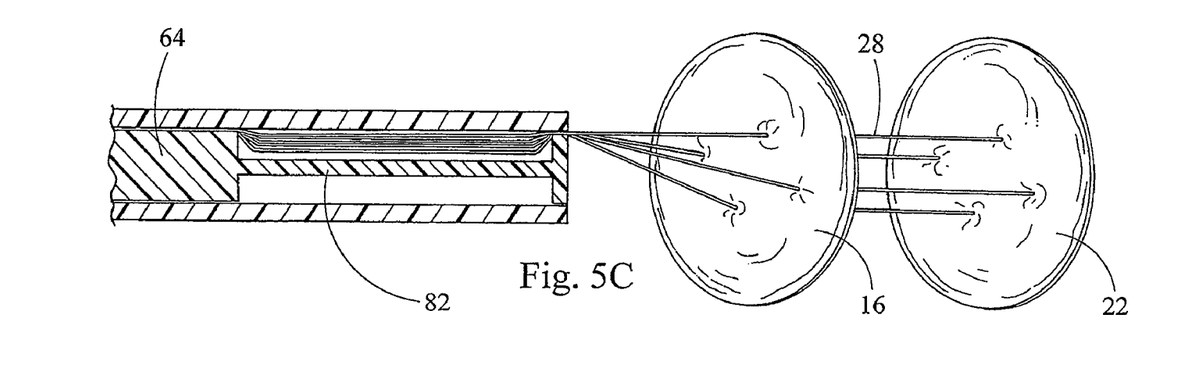
FIG. 5C illustrates the closure device assembly of FIG. 5A deploying a second bioremodelable patch according to an aspect of the present invention.

The pusher 64 may include a bipartite structure configured to separately house and displace one or more bioremodelable patches. In one embodiment, a bipartite pusher includes two displacement/engagement portions linked by a longitudinal core. FIG. 5A-5C shows an exemplary assembly 40 employing a bipartite pusher 64 having two displacement portions 70 and 76 connected by a longitudinal core 82 extending through a proximally disposed patch 16. This assembly 40 includes a proximal, first displacement portion 70 having a substantially larger filled lumen portion than the distal, second displacement portion 76, each displacement portion 70 and 76 directly engaging and displacing a corresponding bioremodelable patch 16 and 22, respectively. The longitudinal core in a bipartite pusher may extend through the bioremodelable patch or around (or over) the patch. Each pusher displacement portion is configured to directly engage and displace a corresponding patch. Accordingly, when the pusher 64 is advanced toward the open distal end 58, it sequentially dislodges the patches 16 and 22, whereby the distal displacement portion 76 dislodges the more distal patch 22 first (FIG. 5B) and the proximal displacement portion 70 dislodges the more proximal patch 16 last (FIG. 5C).

Figure 6:
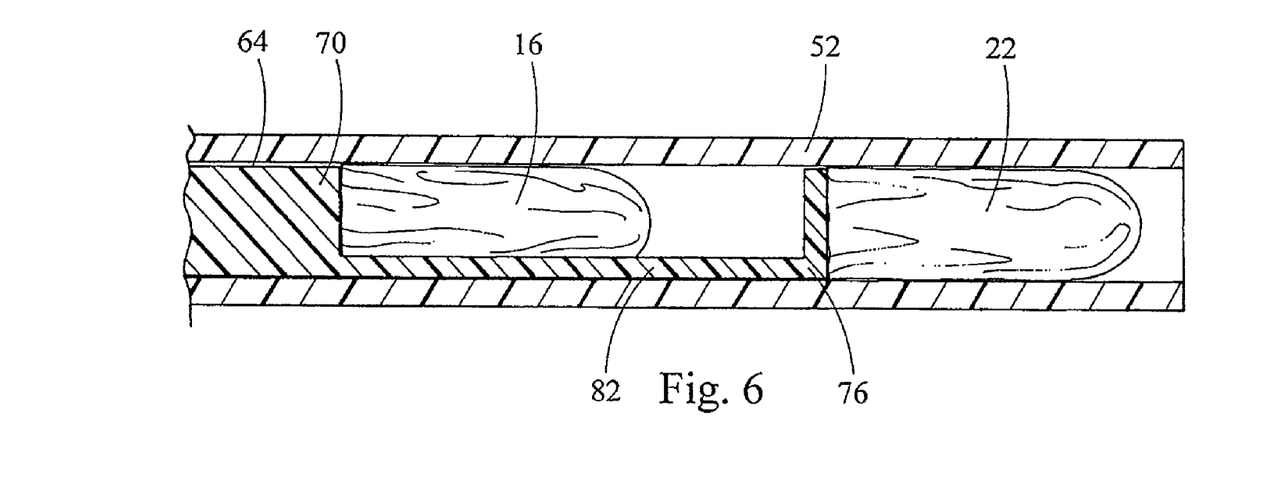
FIG. 6 illustrates a cross-sectional view of an exemplary closure device assembly according to another embodiment of the present invention.

FIG. 6 shows an alternate assembly employing a bipartite pusher in which the longitudinal core 82 connecting the pusher displacement portions 70 and 76 is oriented below (or alongside) the proximal patch 16. As in FIGS. 5A-5C, each pusher displacement portion 70 and 76 is configured to directly engage and sequentially displace a corresponding bioremodelable patch 16 and 22, respectively.

The bioremodelable patches may be compressively joined to a target occlusion site by knotting the sutures to at least one side of the patch or opening. Preferably, the sutures are longer than the distance between the target occlusion site and the site of device entry. Upon suitable placement of bioremodelable patches on either side of a bodily opening or target occlusion site, a knot pushing device may be employed to push a knot toward the occlusion site and to compressively join the bioremodelable patches to one another and/or to tissue portions surrounding the target occlusion site. Any suitable knot pushing device may be used. Suitable knot tying instruments are described in U.S. Pat. No. 5,601,576 and in the U.S. patents cited in the Background section therein.

Upon placement of the patches on either side of a bodily opening, a knot pushing device may be used to push one or more preformed knots to the target occlusion site, cinching the preformed knot(s) to one side of the compressively joined patches. Preferably the sutures are tied extracorporeally using conventional knots, including but not limited to slip knots, single overland knots, clinch knots, sliding knots, bowline knots, half-hitch knots and the like. Tails extending from the knot may be severed using a suitable cutting instrument, such as a bioptome or other suitable cutting instruments known in the surgical arts.

To prevent entanglement of individual sutures linking a pair of patches, sutures extending toward the distal patch may be separated from those extending back toward the proximal patch by the use of one or more inner luminal or inner catheter coaxially positioned within the sheath as described, for example, in U.S. Pat. No. 5,643,317. In particular, one or more sutures may be connected at one of two ends to a proximal end of the catheter, extending though the pair of patches toward the distal end of the catheter and routed back through the catheter for attachment to a ring. The ring can be pulled to compressively engage the patches to one another and to tighten the knot.

The use of a single bioremodelable patch is also contemplated, whereby the patch is sutured or attached to one side of a passageway where occlusion is desired. For example, the outer periphery of a bioremodelable patch may be sutured and knotted to tissues surrounding the passageway using a suturing device. Suitable suturing devices are described in U.S. Pat. No. 5,601,576 and US 2005/0070923. Alternatively, a tissue adhesive may be used to attach the outer periphery of the patch may be attached to tissues surrounding one side of the passageway.

In a further aspect, the present invention provides a method for closing or occluding a bodily opening in a patient using a closure device 10 or closure device assembly as described above. In a preferred embodiment, a method for occluding a PFO opening using the above described closure device assembly is provided. Briefly, the catheter of the closure device assembly is positioned in a septal opening. The pusher is advanced to deploy one or more bioremodelable patches proximate to one or both sides of the septal opening and the bioremodelable patches are secured by the joining element(s) to tissue portion(s) surrounding the septal opening. Preferably, the bioremodelable patches contain an amount of bioremodelable material sufficient to facilitate stable absorption and replacement of the closure device by host tissues upon implantation in a host. In addition, the joining elements are preferably configured for passage through the septal opening, rather than tissue portions adjacent thereto.

Figure 7A:
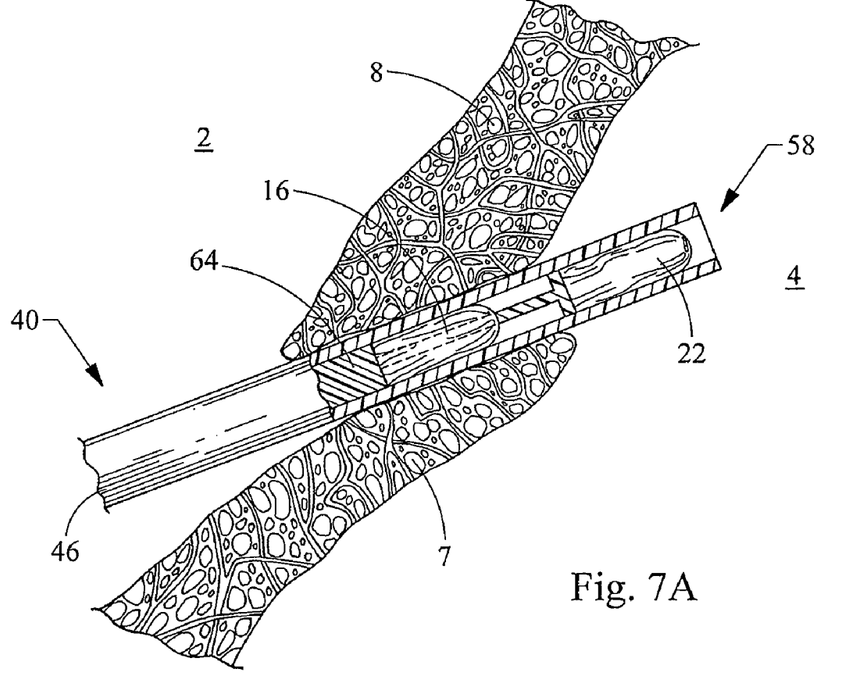
FIG. 7A illustrates a cross-sectional view of the distal end of the closure device assembly of FIG. 5A inserted and extending through a PFO.
Figure 7B:
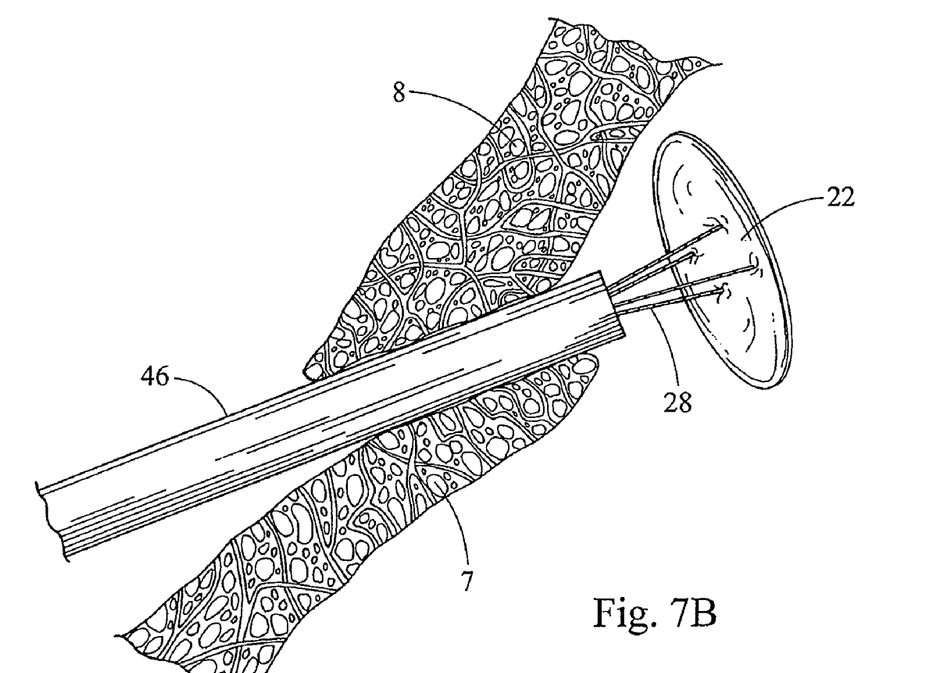
FIG. 7B illustrates a cross-sectional view of the distal end of the closure device assembly of FIG. 5B extending through a PFO and deploying a bioremodelable patch to the left side of the opening.
Figure 7C:
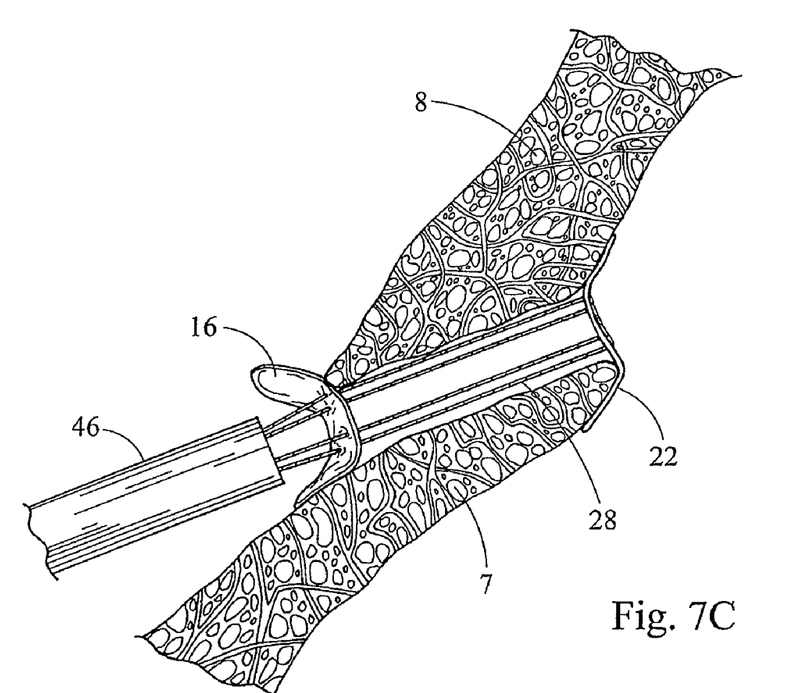
FIG. 7C illustrates a cross-sectional view of the distal end of the closure device assembly of FIG. 5C extending through a PFO and deploying a second bioremodelable patch to the right side of the opening.
Figure 7D:
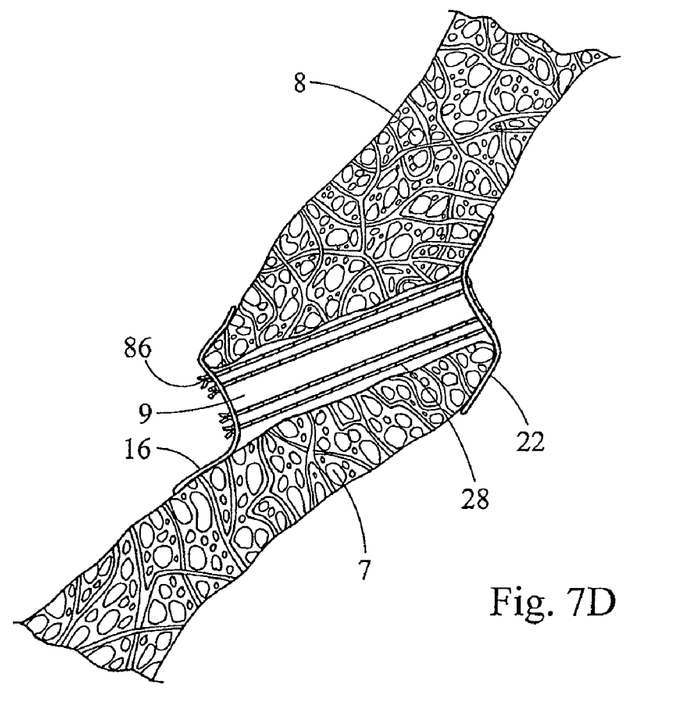
FIG. 7D illustrates a cross-sectional view illustrating a deployed closure device closing a PFO.

By way of example, FIGS. 7A-7D depict a method for closing a PFO. In this case, the catheter 46 is inserted into the right atrium 2, through the PFO 9 between the septum primum 7 and the septum secundum 8, and into the left atrium 4 (FIG. 7A). The pusher 64 is advanced to deploy a first bioremodelable patch 22 into the left atrium 4 (FIG. 7B). The catheter 46 may then be drawn back into the right atrium 2, wherein the pusher 64 is further advanced to deploy a second bioremodelable patch 16 into the right atrium 2 (FIG. 7C). The patches 16 and 22 may be secured to overlapping septum primum 7 and septum secundum 8 tissue portions by cinching each suture 28 with one or more knots 86 to at least one side of the PFO 9, thereby closing the PFO 9 (FIG. 7D).

Upon suitable placement of each bioremodelable patch on either side of a bodily opening or target occlusion site, a knot pushing device may be used to push one or more knots toward the occlusion site. A sufficient force may then be applied to cinch the knot(s) to one side of opening. Any suitable knot pushing device may be used. Suitable knot tying instruments are described in U.S. Pat. No. 5,601,576 and in the U.S. patents cited in the Background section therein.

Preferably, the sutures 28 are longer than the distance between the target occlusion site and the site of device entry, extending from the assembly 40 beyond the point of device entry. The sutures 28 in the closure device 10 may carry preformed knots and/or extracorporeally tied using conventional knots, including but not limited to slip knots, single overland knots, clinch knots, sliding knots, bowline knots, half-hitch knots and the like. Tails extending from the knot may be severed using a suitable cutting instrument, such as a bioptome or any other suitable cutting instrument known in the surgical arts. Upon cinching the knots 86 and cutting the tails, the patches 16 and 22 are secured to overlapping septum primum 7 and septum secundum 8 tissue portions, thereby closing the PFO 9.

Visualization of the assembly 40 within the interior of the heart may be provided by various means. For example, an ultrasonic probe is positioned in the patient's esophagus, on the surface of the patient's chest, or in the chest cavity adjacent or in contact with the exterior of the heart to ultrasonically image the interior of the heart. Alternatively, an endoscope with a translucent bulb or balloon over its distal end may be introduced into the heart through the closure device assembly and/or through a separate incision in the wall of the heart to allow video-based or direct visualization of the interior of the heart. An angioscope introduced into the heart endovascularly through a peripheral vessel may also be used for intracardiac visualization. Fluoroscopy may provide an additional means for visualization.

Marker materials may be added to one or more components of the closure device and/or assembly so as to render them radiopaque or MRI compatible. In particular, radiopaque fillers, marker bands or powders may be included into one or more of the bioremodelable patches or joining elements to facilitate radiographic visualization of the device during the implantation process. Exemplary radiopaque marker materials include but are not limited to, platinum, gold, tungsten, tantalum, tantalum powder, bismuth, bismuth oxychloride, barium, barium sulphate, iodine and the like.

The radiopaque marker materials may be included within any aspect of the closure device or assembly, including one or more of the patches, joining elements and/or bioremodelable materials. Radiopaque markers may be introduced in any form suitable for the rendering the closure device radiopaque or MRI compatible. In addition, the radiopaque materials can be incorporated in the closure device by a variety of common methods, such as adhesive bonding, lamination between two material layers, vapor deposition, and the materials and methods described in U.S. 2003/0206860, the disclosure of which is incorporated herein by reference.

A closure device 10 or assembly 40 according to the present invention is particularly suited for closing septal heart defects, including PFOs and other atrial septal or ventricular septal defects. However, the closure device 10 can be similarly applied to closing or occluding a variety of other heart openings, tissue openings, vessels, vessel punctures, ducts, and other tissue openings where occlusion is desired.

It is intended that the foregoing detailed description be regarded as illustrative rather than limiting, and that it be understood that it is the following claims, including all equivalents, that are intended to define the spirit and scope of this invention.

The invention claimed is:

1. A closure device assembly comprising:
   a catheter having a hollow sheath and an open distal end; a pusher slidably disposed in the hollow sheath;
   a proximal bioremodelable patch and a distal bioremodelable patch co-disposed in the sheath, each patch having a plurality of perforations spaced apart from each other; and
   at least two joining elements; wherein one joining element extends through a first perforation of the first bioremodelable patch and through a first perforation of the second bioremodelable patch, and another joining element extends through a second perforation of the first bioremodelable patch and through a second perforation of the second bioremodelable patch;
   wherein the pusher is configured to sequentially dislodge the proximal and distal bioremodelable patches and the joining elements from the open distal end near the bodily opening,
   wherein the pusher comprises first and second displacement portions connected by a longitudinal core, the first displacement portion having a distal surface that engages a proximal surface of the proximal bioremodelable patch, and the second displacement portion having a distal surface that engages a proximal surface of the distal bioremodelable patch, and wherein the longitudinal core passes to one side of the proximal bioremodelable patch.

2. The device of claim 1, wherein the at least two joining elements comprises sutures.

3. The device of claim 1, wherein the at least one joining element further comprises a tissue adhesive.

4. The device of claim 1, wherein the at least two bioremodelable patches a bioactive agent configured to stimulate angiogenesis.

5. The device of claim 1, wherein the at least two bioremodelable patches comprise a collagenous extracellular matrix material.

6. The device of claim 1, wherein the at least two bioremodelable patches comprises submucosal tissue material.

7. The device of claim 1, wherein the at least two bioremodelable patches comprises non-submucosal tissue material.

8. The device of claim 1, wherein the at least two bioremodelable patches are substantially formed from bioremodelable material.

9. The device of claim 1, wherein the at least two joining members are sutures that are configured to be-compressively joined the first and second bioremodelable patches to opposing tissue portions surrounding a PFO opening.

* * * * *

UNITED STATES PATENT AND TRADEMARK OFFICE
CERTIFICATE OF CORRECTION

| | | |
|---|---|---|
| PATENT NO. | : 8,029,532 B2 | Page 1 of 1 |
| APPLICATION NO. | : 11/869499 | |
| DATED | : October 4, 2011 | |
| INVENTOR(S) | : Daniel J. Sirota | |

It is certified that error appears in the above-identified patent and that said Letters Patent is hereby corrected as shown below:

In the Claims

In column 14, claim 2, line 33, before "sutures." replace "comprises" with --comprise--.

In column 14, claim 4, line 37, after "modelable patches" insert --comprise--.

In column 14, claim 6, line 43, after "modelable patches" replace "comprises" with --comprise--.

In column 14, claim 7, line 45, after "modelable patches" replace "comprises" with --comprise--.

In column 14, claim 9, line 51, replace "be-compressively" with --be compressively--.

Signed and Sealed this
Thirty-first Day of January, 2012

David J. Kappos
*Director of the United States Patent and Trademark Office*